United States Patent
Yamamoto (12)

(10) Patent No.: US 6,180,101 B1
(45) Date of Patent: Jan. 30, 2001

(54) REMEDY FOR AXILLARY OSMIDROSIS CONTAINING ADRENOCORTICOSTEROIDAL PREPARATION

(76) Inventor: Keiko Yamamoto, Yoyogi Park Homes 203, 35-12, Yoyogi 5-chome, Shibuya-ku, Tokyo 151-0053 (JP)

(*) Notice: Under 35 U.S.C. 154(b), the term of this patent shall be extended for 0 days.

(21) Appl. No.: 09/319,691

(22) PCT Filed: Dec. 10, 1996

(86) PCT No.: PCT/JP96/03606

§ 371 Date: Oct. 5, 1999

§ 102(e) Date: Oct. 5, 1999

(87) PCT Pub. No.: WO98/25624

PCT Pub. Date: Jun. 18, 1999

(51) Int. Cl.⁷ .............................. A61K 7/32; A61K 35/00; A61K 31/56; A01N 63/02; C07J 5/00

(52) U.S. Cl. ............................ 424/115; 424/401; 424/65; 424/93.3; 424/93.4; 424/93.45; 552/576; 514/179

(58) Field of Search ............................ 424/401, 65, 93.3, 424/93.4, 93.45, 115; 552/576; 514/179

(56) References Cited

FOREIGN PATENT DOCUMENTS

| 63-179829 | 7/1988 | (JP) . |
| 366608 | 3/1991 | (JP) . |

*Primary Examiner*—Francisco Prats
*Assistant Examiner*—Susan D. Coe
(74) *Attorney, Agent, or Firm*—Liniak, Berenato, Longacre & White

(57) ABSTRACT

A remedy for tragomaschalia characterized in that it conntains an effective amount of adrenocorticosteroid and from 1 to 10% by weight of an extraction product from lactic acid fermentation based on one gram of a base. The extraction product from lactic acid fermentation has a metabolism product of lactic acid bacteria and ingredients of bacterial cells of lactic acid bacteria together. By inhibition of the secretion itself of a odoriferous steroid which is the cause of tragomaschalia, remetabolism and generation of such a steroid compound by tragomaschalia bacteria are completely eliminated, and there is little fear of adverse drug reactions by the adrenocorticosteroid used for that purpose.

3 Claims, No Drawings

REMEDY FOR AXILLARY OSMIDROSIS CONTAINING ADRENOCORTICOSTEROIDAL PREPARATION

TECHNICAL FIELD

The present invention concerns a remedy for tragomaschalia using an adrenocorticosteroidal preparation and, more in particular, it relates to a remedy for tragomaschalia using the adrenocorticosteroidal preparation in combination with an extraction product from lactic acid fermentation.

BACKGROUND ART

Various attempts have been made so far as countermeasures or treatments for tragomaschalia, such as elimination of odor by deodorants, suppression of an environment for bacterial multiplication by antiperspirants and inhibition of bacterial activity and sterilization by antibacterial substances such as antibiotics or bactericides.

Steroid secretory epithelial tissues such as aporine glands attributable to tragomaschalia metabolize and secretes various steroid compounds such as cholesterol and sex hormone.

A kind of steroid compound among them is metabolized by bacterial flora that have rooted and multiplied on the axilla epithelium, thus producing an odoriferous steroid compound 5α-androst-16-en-3-on(5α-A), which causes tragomaschalia. The compound itself however has not been detected in secretions from the secreting tissues concerning tragomaschalia. A general theory suggests that a $C_{19}$ steroid compound metabolized and produced in the secretory tissues may be metabolized again and produced by the bacteria rooted in the underarm.

Among the bacteria rooted on epithelia, many propionibacteria or coryneform bacteria and some of staphylococci include species having a steroid metabolism function.

Conventional countermeasures against tragomaschalia have mainly been performed by inhibiting the production of odoriferous steroid by axilla application of antibiotics, to remove bacteria rooted on the axilla epithelia. The effects however are only temporary, and tragomaschalia can be eradicated at present only by a surgical treatment.

The inventors had studied on the subject of finding a remedy capable of rapidly eradicating tragomaschalia without any surgical treatment and, as a result, found it effective to combine an adrenocorticosteroid and an antibacterial substance as a supplemental agent, which has already been proposed (Japanese Patent Unexamined Publication Hei 3-66608).

Adrenocorticosteroidal preparations have not been used at all for treating tragomaschalia and, therefore, concrete pharmaceutical actions of them against tragomaschalia have not yet been clear, but it is supposed that they are due to the sensitivity of propionibacteria to adrenocorticosteroids and, particularly, due to the inhibition of secretion of causal substances for the odoriferous steroid from the axillary epithelial tissues caused by the action of inhibiting living tissues to synthesize and secrete steroids, which is one of physiological actions of adrenocorticosteroids.

The therapeutic effects of the adrenocorticosteroidal preparation for tragomaschalia are extremely remarkable and rapid, and our initial clinical experiments had revealed that several times of application of an effective amount of not more than about 2 mg can heal tragomaschalia very effectively though it depended on symptoms. However, a steroidal preparation itself might possibly cause adverse drug reactions by continuous use, and it is preferable to use it at a high concentration and for a period as short as possible. The dose however was limited since adverse drug reactions such as eczema, erosion and also lichenoid change might occur if the frequency of administration was increased in accordance with constitutions and symptoms, and infectious diseases might also occur in combination.

DISCLOSURE OF THE INVENTION

The inventors have made various experiments taking notice on the fact that metabolism products of lactic acid bacteria obtained by lactic acid fermentation not only have an astriction or reparative action on skins but also shows a bacteriostatic or bacteriocidal action against bacteria, and have found that the use of an adrenocorticosteroid showing a specific therapeutic effect against tragomaschalia in combination with a particular extraction product obtained by lactic acid fermentation substantially inhibits the adverse drug reaction of the adrenocorticosteroid.

That is, the present invention provides a remedy for tragomaschalia characterized in that it contains an effective amount of an adrenocorticosteroid and from 1 to 10% by weight of an extraction product from lactic acid fermentation based on a base (1 g).

BEST MODE FOR CARRYING OUT THE INVENTION

Although an adrenocorticosteroid has a significant effect on propionibacteria, a cause for tragomaschalia, already at a concentration of about 100 ppm based on a base it is preferred to use It at a concentration at least of 300 ppm as a practical remedy for tragomaschalia. On the other hand, administration at a concentration in excess of about 30,000 ppm (30 mg/g) no more increases the effect.

The adrenocorticosteroidal preparations used for the present invention include many commonly known adrenocorticosteroidal preparations showing a similar effect such as prednisolone, cortisone, cortisol, hydrocortisone, prednisone, methylprednisone, methylprednisolone, triamcinolone, dexamethasone, paramethasone, betamethasone and beclomethasone.

On the other hand, adverse drug reactions by such adrenocorticosteroids are remarkably inhibited by the extraction products from lactic acid fermentation. Although the reason is not always clear, it is supposed that the extraction products not only prevent occurrence of skin disorder induced as an adverse drug reaction of the adrenocorticosteroid but also recover the lesion and change of the skins to normal states to inhibit induction of infectious diseases.

The extraction product is used within a range from 1 to 10% by weight based on a base. An intended effect is observed already at 1% by weight and the effect increases with the increase of the concentration, but a stimulative feeling to skins is increased to disturb practical therapy if it exceeds 10% by weight.

As the extraction product by lactic acid fermentation of the present invention, it is preferred to use a mixture of an extraction product obtained from lactic acid fermentation, particularly, a purified lactic acid solution obtained by a heat sterilization and filtration with a membrane filter of a lactic acid fermentation liquid, and an extraction product derived from cytoplasms of bacterial cells obtained by milling lactic acid bacterial cells as a cake.

The extraction products obtained from lactic acid fermentation contain a metabolism product (lactic acid) released from bacterial cells and, in addition, various kinds of amino acids, proteins, nucleic acids, lipids, glycoproteins and polysaccharides derived from the constituents of the bacterial cells, and they are collectively referred to as the extraction product from lactic acid fermentation.

The lactic acid bacteria used in the present invention have a feature in that they are of bacteria strains selectively obtained by simultaneous culturation of different multiple kinds of lactic acid bacteria in a step of mutual competitive growth.

Lactic acid bacteria used for the present invention include various species, and culturing methods therefor are also varied. For example, a preferred result is obtained by primary culturation of a multiplicity strains of lactic acid bacteria in each of groups (I) to (IV), containing at least one strain of lactic acid bacillus and one strain of lactic acid micrococcus in each group, the bacteria strains being different between each of the groups, namely, I (*B. bulgaricus A, B. acidophilus 1, M. lactisacidi*), II (*B. bulgaricus B, B. acidophilus, M. lactisacidi*), III (Kornchenbacillus A, *B. acidophilus, M. lactisacidi*) and IV (Kornchenbacillus B, *B. acidophilus, W. lactisacidi*), separately under a predetermined condition on every group, and then further simultaneous secondary culturation by collecting the thus obtained culturation products of respective groups together. Preferably, in this case, the metabolism products in the primary culturation are removed by filtration and only the bacterial cells are cultured in the secondary culturation.

When the lactic acid bacteria obtained by the secondary culturation are treated, for example, by heat sterilization and the metabolism products released during the culturation to the outside of the bacterial cells are separated by filtration with a membrane filter under vacuum, a transparent acidic liquid (pH 3–4) (lactic acid) is obtained as filtrates. The extraction products from lactic acid fermentation are obtained by addition of the ingredients of the constituent substances derived from the bacterial cells obtained by milling of and extraction from the bacterial cells as a cake on the filter.

EXAMPLE

The invention will be described below by way of examples.

Example 1

87 kg of purified water were added to 10 kg of skimmilk powder and 3 kg of glucose, and the mixture was sterilized by heating at 100° C. for 60 minutes then cooled to 37° C. to prepare a culture medium. Then lactic acid bacteria prepared separately (*Streptococcus thermophilus*) were inoculated and cultured at 37° C. for 48 hours. The cultured solution was heated to 60° C. to sterilize, then filtered through Celite and further subjected to sterile filtration using a membrane filter, to obtain a fermented lactic acid solution as a transparent filtrate at pH of about 3 to 4. Furthermore, the lactic acid bacterial cells as a cake on the filter were frozen and milled to obtain extraction products derived from the cytoplasms of the bacterial cells, which were mixed with the lactic acid solution to obtain an extraction product A from lactic acid fermentation.

Example 2

The groups (I)–(IV) of lactic acid bacteria, with strains being different between each of the groups divided into each of: I (*B. bulgaricus A, B. acidophilus, M. lactisacidi*), II (*B. bulgaricus B, B. acidophilus, M. lactisacidi*), III (Kornchenbacillus A, *B. acidophilus, M. lactisacidi*) and IV (Kornchenbacillus B, *B. acidophilus, W. lactisacidi*) were respectively cultured under the condition at an average temperature of about 37° C. for 120 hours using a culture medium for lactic acid bacteria of the following composition:

| | |
|---|---|
| Trypticase peptone | 10.000 g |
| Yeast extract | 5.000 g |
| Potassium phosphate | 6.000 g |
| Ammonium citrate | 2.000 g |
| Glucose | 20.000 g |
| Sorbitan monooleate | 1.000 g |
| Hydrated sodium acetate | 25.000 g |
| Magnesium sulfate | 0.575 g |
| Manganese sulfate | 0.120 g |
| Ferrous sulfate | 0.034 g |
| Agar | 15.000 g |
| pH 5.5 | |

The culturation products obtained were treated in the same manner as in Example 1 to obtain an extraction product B from lactic acid fermentation.

Example 3

Sensitivity Test of Propionibacterium Acnes to Adrenocorticosteroidal Preparation Test bacteria prepared by subculture were inoculated to a growth medium and was cultured at 35° C. for 48 hours under an anaerobic condition. Then the liquid culture was diluted with the growth medium so that the bacterium count was about $10^6$/ml, and a platinum loop amount of the bacterial cell was transferred to a GAM bouillon (Nissui Seiyaku Co., Ltd.) and was cultured at 35° C. for 24 hours under an anaerobic condition to prepare a bacterium solution for inoculation.

The bacterium solution was dispensed to respective Petri dishes containing GAM agar medium (Nissui Seiyaku Co., Ltd.), each by 15 ml, so that the bacterial count was about $10^6$/ml and the solution was fixed. Then, a test piece containing prednisolone as an adrenocorticosteroidal preparation at a concentration of 28 mg based on one gram of a base cream, and the piece was further diluted stepwise with the cream to 1–28,000 times respectively. Sensitivity discs (filter paper) of 10 mm diameter to each of which the diluted test piece was applied were respectively placed on the culture media. A halo (growth inhibition circle) was observed when the culturation was completed after a predetermined time. The results are shown in the table below. As can be seen from the table, the formation of the halo (4 mm) was already observed at a dilution factor of about 280 (1000 ppm). The width W of the halo is given by an expression: W=T-D/2, where T is the width of an inhibition band including the test piece and D is the width of the test piece. Formation of Halo (growth inhibition band) to Test Bacterium

| Test bacterium | Bacterial concentration (/mL) | Specimen Dilution factor | Effective ingredient Concentration (ppm) | Results |
|---|---|---|---|---|
| Propionibacterium acnes | 4.8 × 10$^6$ | 1 | 28,000 | +(18 mm) |
| | | 7 | 4,000 | +(14 mm) |
| | | 28 | 1,000 | +(11 mm) |
| | | 280 | 100 | +(4 mm) |
| | | 2,800 | 10 | — |
| | | 28,000 | 1 | — |

Example 4

As can be seen from the results of the sensitivity test, propionibacteria already showed a significant sensitivity against the adrenocorticosteroidal preparation at a concentration of 100 ppm, which remarkably increased at a concentration 1000 ppm or higher. A therapeutic experiment was performed in which a test drug comprising a combination of the adrenocorticosteroidal preparation at a concentration of 300 ppm and the extraction product A from lactic acid fermentation at a concentration of 3% by weight was applied to patients suffering from tragomaschalia.

In the experiment, a remedy for tragomaschalia containing 0.3 mg (300 ppm) of prednisolone as the adrenocorticosteroidal preparation and 30 mg of the extraction product A (3% by weight) in 1 g of an ointment cream as a base was applied to 350 patients' underarm once per day by a usual method. Improvements were observed in many patients but, depending on symptoms, there were some cases where the osmidrosis once reduced or eliminated reappeared in about one week, so that the concentration of prednisolone for this application was effective to some extent, but it was not enough depending on the symptoms.

Example 5

A similar application treatment was performed on 150 patients suffering from tragomaschalia by using a cream prepared by mixing prednisolone at a concentration of 28 mg (28000 ppm) and 30 mg of the extraction product B in 1 g of a base. No recurrences were found in most of the patients for a long period. No adverse drug reactions attributable to prednisolone were observed.

In this test, by previous repetitive administration of a usual adrenocorticosteroidal preparation as a therapy for atopy, the patients had already suffered from eczema, anthema and erosion on the skins in the axillay region as an adverse drug reaction before the treatment for tragomaschalia.

The cream was applied to these patients during the experiment twice to 4 times per day depending on the symptoms. As a result, the dermatoses due to the adverse drug reaction were remarkably reduced in 8 patients, and were completely cured in 2 patients and neither tragomaschalia nor dermatoses have recurred yet. In other two out of ten patients, since no effects were recognized, the application was discontinued.

INDUSTRIAL APPLICABILITY

According to the present invention, remarkable therapeutic effects are recognized by medication in a short period on tragomaschalia which have been conventionally considered difficult to be eradicated. Little adverse drug reactions by the adrenocorticosteroidal preparation used are recognized. The present invention therefore has an effective application use as a remedy for tragomaschalia.

What is claimed is:

1. A composition for treating tragomaschalia comprising an effective amount of an adrenocorticosteroid and from 1 to 10% by weight of an extraction product from lactic acid fermentation based on one gram of said composition, wherein the extraction product from a lactic acid fermentation is a mixture of a metabolism product formed from bacterial cells during culturation of lactic acid bacteria which is obtained as a liquid filtrate from sterilized bacterial cells through filtration and components derived from the cytoplasm of bacterial cells obtained by milling filtration residue of the bacterial cells after filtration.

2. A composition for treating tragomaschalia as defined in claim 1, wherein said composition contains the adrenocorticosteroid within a range of from 0.3 to 30 mg.

3. A composition for treating tragomaschalia as defined in claim 1, wherein the lactic acid bacteria are obtained by primary culturation of a multiplicity of groups of lactic acid bacteria, with the strain being different between each of the groups, and by subsequent secondary culturation taken place by culturing once cured lactic acid bacteria in each of the groups collectively.

* * * * *